US00PP26104P2

(12) United States Plant Patent
Barends

(10) Patent No.: US PP26,104 P2
(45) Date of Patent: Nov. 17, 2015

(54) PELARGONIUM PLANT NAMED 'FIPELDANBURG'

(50) Latin Name: *Pelargonium peltatum*
Varietal Denomination: Fipeldanburg

(71) Applicant: Eveline Barends, De Lier (NL)

(72) Inventor: Eveline Barends, De Lier (NL)

(73) Assignee: Fides B.V., De Lier (NL)

( * ) Notice: Subject to any disclaimer, the term of this patent is extended or adjusted under 35 U.S.C. 154(b) by 161 days.

(21) Appl. No.: 13/998,294

(22) Filed: Oct. 18, 2013

(51) Int. Cl.
*A01H 5/02* (2006.01)

(52) U.S. Cl.
USPC ..... Plt./332

(58) Field of Classification Search
USPC ..... Plt./332
See application file for complete search history.

*Primary Examiner* — Anne Grunberg
(74) *Attorney, Agent, or Firm* — C. A. Whealy

(57) ABSTRACT

A new and distinct cultivar of *Pelargonium* plant named 'Fipeldanburg', characterized by its upright to outwardly spreading and uniformly mounding plant habit; freely basal branching habit; early and freely flowering habit; semi-double burgundy-colored flowers; and good garden performance.

1 Drawing Sheet

Botanical designation: *Pelargonium peltatum.*
Cultivar denomination: 'FIPELDANBURG'.

BACKGROUND OF THE INVENTION

The present invention relates to a new and distinct cultivar of *Pelargonium* plant, botanically known as *Pelargonium peltatum*, commonly referred to as Ivy Geranium, and hereinafter referred to by the name 'Fipeldanburg'.

The new *Pelargonium* plant is a product of a planned breeding program conducted by the Inventor in De Lier, The Netherlands. The objective of the breeding program is to create new freely-branching and freely-flowering *Pelargonium* plants with large flowers and attractive leaf and flower coloration.

The new *Pelargonium* plant originated from a cross-pollination made by the Inventor in September, 2006 in De Lier, The Netherlands of a proprietary selection of *Pelargonium peltatum* identified as code number 60011, not patented, as the female, or seed, parent with a proprietary selection of *Pelargonium peltatum* identified as code number 88873, not patented, as the male, or pollen, parent. The new *Pelargonium* plant was discovered and selected by the Inventor as a single flowering plant from within the progeny of the stated cross-pollination in a controlled greenhouse environment in De Lier, The Netherlands in March, 2007.

Asexual reproduction of the new *Pelargonium* plant by vegetative terminal cuttings in a controlled greenhouse environment in De Lier, The Netherlands since July, 2007 has shown that the unique features of this new *Pelargonium* plant are stable and reproduced true to type in successive generations.

SUMMARY OF THE INVENTION

Plants of the new *Pelargonium* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Fipeldanburg'. These characteristics in combination distinguish 'Fipeldanburg' as a new and distinct *Pelargonium* plant:

1. Upright to outwardly spreading and uniformly mounding plant habit.
2. Freely basal branching habit.
3. Early and freely flowering habit.
4. Semi-double burgundy-colored flowers.
5. Good garden performance.

Plants of the new *Pelargonium* differ primarily from plants of the female parent selection in flower color as plants of the female parent selection have pink-colored flowers.

Plants of the new *Pelargonium* differ primarily from plants of the male parent selection in flower form as flowers plants of the male parent selection are single types with five petals.

Plants of the new *Pelargonium* can be compared to plants of *Pelargonium peltatum* 'Global Merlot', disclosed in U.S. Plant Pat. No. 11,733. In side-by-side comparisons conducted in De Lier, The Netherlands, plants of the new *Pelargonium* differed primarily from plants of 'Global Merlot' in the following characteristics:

1. Plants of the new *Pelargonium* had larger leaves than plants of 'Global Merlot'.
2. Flower umbels of plants of the new *Pelargonium* were denser than and not as open as flower umbels of plants of 'Global Merlot'.
3. Flowers of plants of the new *Pelargonium* were slightly darker in color than flowers of plants of 'Global Merlot'.

BRIEF DESCRIPTION OF THE PHOTOGRAPH

The accompanying colored photograph illustrates the overall appearance of the new *Pelargonium* plant showing the colors as true as it is reasonably possible to obtain in colored reproductions of this type. Colors in the photograph may differ slightly from the color values cited in the detailed botanical description which accurately describe the colors of the new *Pelargonium* plant.

The photograph comprises a side perspective view of a typical flowering plant of 'Fipeldanburg' grown in a container.

DETAILED BOTANICAL DESCRIPTION

The aforementioned photograph and following observations, measurements and values describe plants grown during the summer in 10.5-cm containers in a glass-covered greenhouse in De Lier, The Netherlands and under cultural practices typical of commercial *Pelargonium* production. During the production of the plants, day temperatures ranged from 16° C. to 28° C. and night temperatures ranged from 14° C. to 18° C. Plants were ten weeks old when the photograph was taken and 20 weeks old when the description was taken. In the detailed description, color references are made to The Royal Horticultural Society Colour Chart, 2007 Edition, except where general terms of ordinary dictionary significance are used.

Botanical classification: *Pelargonium peltatum* 'Fipeldanburg'.

Parentage:

*Female, or seed, parent*.—Proprietary selection of *Pelargonium peltatum* identified as code number 60011, not patented.

*Male or pollen parent*.—Proprietary selection of *Pelargonium peltatum* identified as code number 88873, not patented.

Propagation:

*Type*.—By vegetative terminal cuttings.

*Time to initiate roots, summer*.—About four days at temperatures about 22° C.

*Time to initiate roots, winter*.—About one week at temperatures about 22° C.

*Time to produce a rooted young plant, summer*.—About 16 days at temperatures about 22° C. to 30° C.

*Time to produce a rooted young plant, winter*.—About three weeks at temperatures about 20° C. to 25° C.

*Root description*.—Medium in thickness, fibrous; whitish grey in color.

*Rooting habit*.—Moderately freely branching, medium density.

Plant description:

*Plant habit*.—Upright to outwardly spreading and uniformly mounding plant habit; densely foliated.

*Growth and branching habit*.—Moderately vigorous growth habit; freely basal branching habit.

*Plant height, to top of umbels*.—About 34 cm to 37 cm.

*Plant height, to top of leaves*.—About 20 cm to 25 cm.

*Plant width*.—About 50 cm to 60 cm.

*Lateral branches*.—Length: About 15 cm to 30 cm. Diameter: About 5.5 mm to 5.6 mm. Internode length: About 2 cm to 6.5 cm. Texture: Pubescent. Strength: Moderately strong. Color: Close to 144A.

Leaf description:

*Arrangement*.—Alternate; simple.

*Length*.—About 5.3 cm to 5.8 cm.

*Width*.—About 8 cm to 10 cm.

*Shape*.—Roughly orbicular; palmately lobed.

*Apex*.—Acute.

*Base*.—Cordate.

*Margin*.—Entire; palmately lobed.

*Venation pattern*.—Palmate.

*Texture, upper surface*.—Smooth, glabrous.

*Texture, lower surface*.—Slightly pubescent; more dense along the veins.

*Color*.—Developing and fully expanded leaves, upper surface: Close to N137B; venation, close to N137B. Developing and fully expanded leaves, lower surface: Close to 146A; venation, close to 146B. Zonation pattern, upper surface only: Location: Towards the base of the leaf. Width: About 2 cm. Color: Close to N147A; actual color will vary with light levels.

*Petiole*.—Length: About 3.5 cm to 6 cm. Diameter: About 2.2 mm. Texture, upper and lower surfaces: Pubescent. Color, upper and lower surfaces: Close to 144A.

Flower description:

*Flower arrangement*.—Semi-double flowers arranged in rounded hemispherical umbels arising from apical leaf axils; umbels displayed above the foliar plane on strong peduncles; flowers face upright to outwardly.

*Fragrance*.—None detected.

*Quantity of flowers*.—Freely flowering habit; about 10 to 16 flowers and flower buds per umbel and about ten to twelve umbels developing per plant.

*Flowering season*.—In The Netherlands, flowering is continuous from late spring until frost in the autumn; early flowering habit, plants begin flowering about six to eight weeks after planting.

*Flower longevity*.—Individual flowers last about 2 to 14 days on the plant; flowers persistent.

*Umbel height*.—About 4.5 cm.

*Umbel diameter*.—About 7 cm to 8 cm.

*Flower diameter*.—About 4.5 cm to 5 cm.

*Flower depth* (*height*).—About 2.2 cm.

*Flower buds*.—Length: About 1.1 cm to 1.5 cm. Diameter: About 5 mm to 10 mm. Shape: Globular to elliptic. Color: Close to 144A.

*Petals and petaloids*.—Quantity per flower: About 22 to 26. Length: About 2.2 cm to 2.5 cm. Width: About 1.1 cm to 1.4 cm. Shape: Spatulate to obovate; smallest petals/petaloids, irregularly obovate to oblanceolate. Apex: Round. Base: Attenuate. Margin: Entire. Texture, upper and lower surfaces: Smooth, glabrous; velvety. Color: When opening, upper surface: Darker than N77A. When opening, lower surface: Close to 75C; towards the base, close to 59A or occasionally almost white. Fully opened, upper surface: Close to between 59A and N77A; color becoming closer to N77A with development. Fully opened, lower surface: Close to 59A; color becoming closer to 70A with development.

*Sepals*.—Quantity per flower: Five arranged in a single whorl. Length: About 1.4 cm to 1.6 cm. Width: About 5 mm. Shape: Lanceolate to acicular. Apex: Acute. Base: Lobate to truncate. Margin: Entire. Texture, upper and lower surfaces: Densely pubescent. Color, upper and lower surfaces: Close to 144A.

*Peduncle* (*umbel stem*).—Length: About 11 cm to 14 cm. Diameter: About 3.5 mm to 4.5 mm. Strength: Strong. Angle: Erect to about 30° C. from vertical. Texture: Pubescent. Color: Close to 144A.

*Pedicel* (*individual flower stem*).—Length: About 2.5 cm. Diameter: About 1.4 mm to 1.6 mm. Strength: Moderately strong. Angle: Erect to about 60° C. from peduncle axis. Texture: Pubescent. Color: Close to 144B.

*Reproductive organs*.—Androecium: Stamen quantity per flower: About one to five. Filament length: About 6 mm to 7 mm. Filament color: Close to 155A. Anther length: About 2 mm to 3 mm. Anther shape: Oblong. Anther color: Close to 39A. Pollen amount: Moderate. Pollen color: Close to 33B. Gynoecium: Pistil quantity per flower: One. Pistil length: About 1.2 cm to 1.4 cm. Stigma shape: Tapering; reflexed. Stigma color: Close to 155A. Style length: About 7 mm to 10 mm. Style color: Close to N74D. Ovary color: Close to 138D.

*Fruits and seeds*.—Fruit and seed development has not been observed on plants of the new *Pelargonium*.

Disease & pest resistance: Plants of the new *Pelargonium* have not been observed to be resistant to pathogens and pests common to *Pelargonium* plants.

Garden performance: Plants of the new *Pelargonium* have been observed to have good garden performance and to tolerate rain, wind and temperatures ranging from about 4° C. to 35° C.

It is claimed:

1. A new and distinct *Pelargonium* plant named 'Fipeldanburg' as illustrated and described.

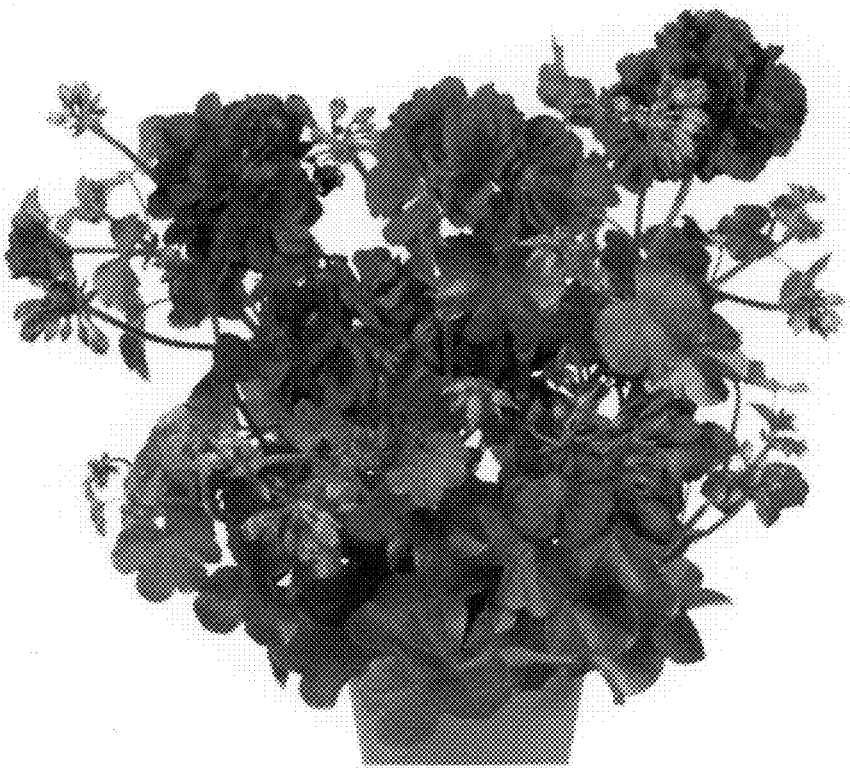

* * * * *